United States Patent [19]
Ferguson et al.

[11] Patent Number: 5,306,264
[45] Date of Patent: Apr. 26, 1994

[54] OSTOMY BAG WITH MULTI-STAGE FILTER

[75] Inventors: Keith Ferguson, Scotch Plains; Mark Lesko, Jackson, both of N.J.

[73] Assignee: E. R. Squibb & Sons, Inc., Princeton, N.J.

[21] Appl. No.: 4,322

[22] Filed: Jan. 14, 1993

[51] Int. Cl.$^5$ ............................................... A61F 5/44
[52] U.S. Cl. .................. 604/333; 604/338; 604/342; 604/332
[58] Field of Search ................. 604/332–345

[56] References Cited

U.S. PATENT DOCUMENTS

| | | | |
|---|---|---|---|
| 4,203,445 | 5/1980 | Jessup et al. | 604/333 |
| 4,387,712 | 6/1983 | Briggs et al. | 604/333 |
| 4,911,699 | 3/1990 | Fenton | 604/333 |

FOREIGN PATENT DOCUMENTS

| | | | |
|---|---|---|---|
| 0082084 | 6/1983 | European Pat. Off. | 604/333 |
| 2247172 | 2/1992 | United Kingdom | 604/333 |

Primary Examiner—Randall L. Green
Assistant Examiner—Rob Clarke
Attorney, Agent, or Firm—Stuart E. Krieger

[57] ABSTRACT

The ostomy bag includes a multi-stage filter system that provides contamination protection for a deodorizing filter in the system. The multi-stage filter system also includes a gas transmissible protection filter that is impassible to semi-liquid waste material. The protection filter is located in the ostomy bag to precede the deodorizing filter such that gaseous waste must pass through the protection filter before it passes through the deodorizing filter. In one embodiment of the invention wherein the ostomy bag has a single chamber, the protection filter is a two layer structure with different pore counts that overlay the deodorizing filter. In another embodiment of the invention wherein the ostomy bag has dual chambers, the protection filter, without overlaying the deodorizing filter, is disposed across the flow path of gaseous waste to the deodorizing filter such that any gaseous waste that reaches the deodorizing filter must flow through the protection filter. Thus semi-liquid waste material cannot contact the deodorizing filter since it cannot bypass the protection filter to reach the deodorizing filter.

20 Claims, 5 Drawing Sheets

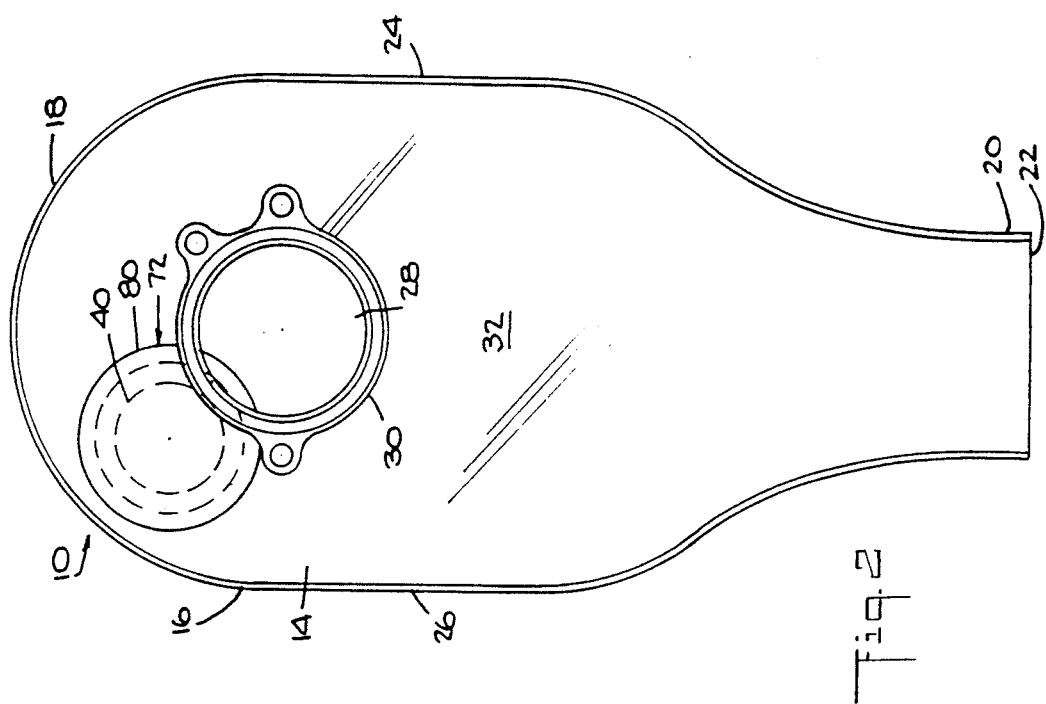
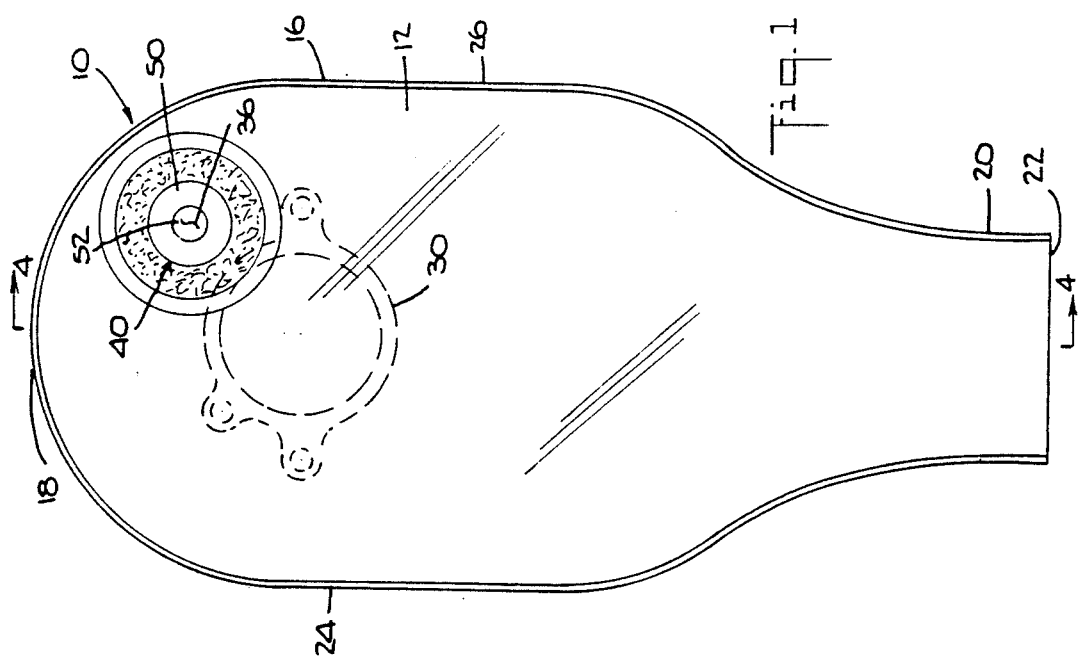

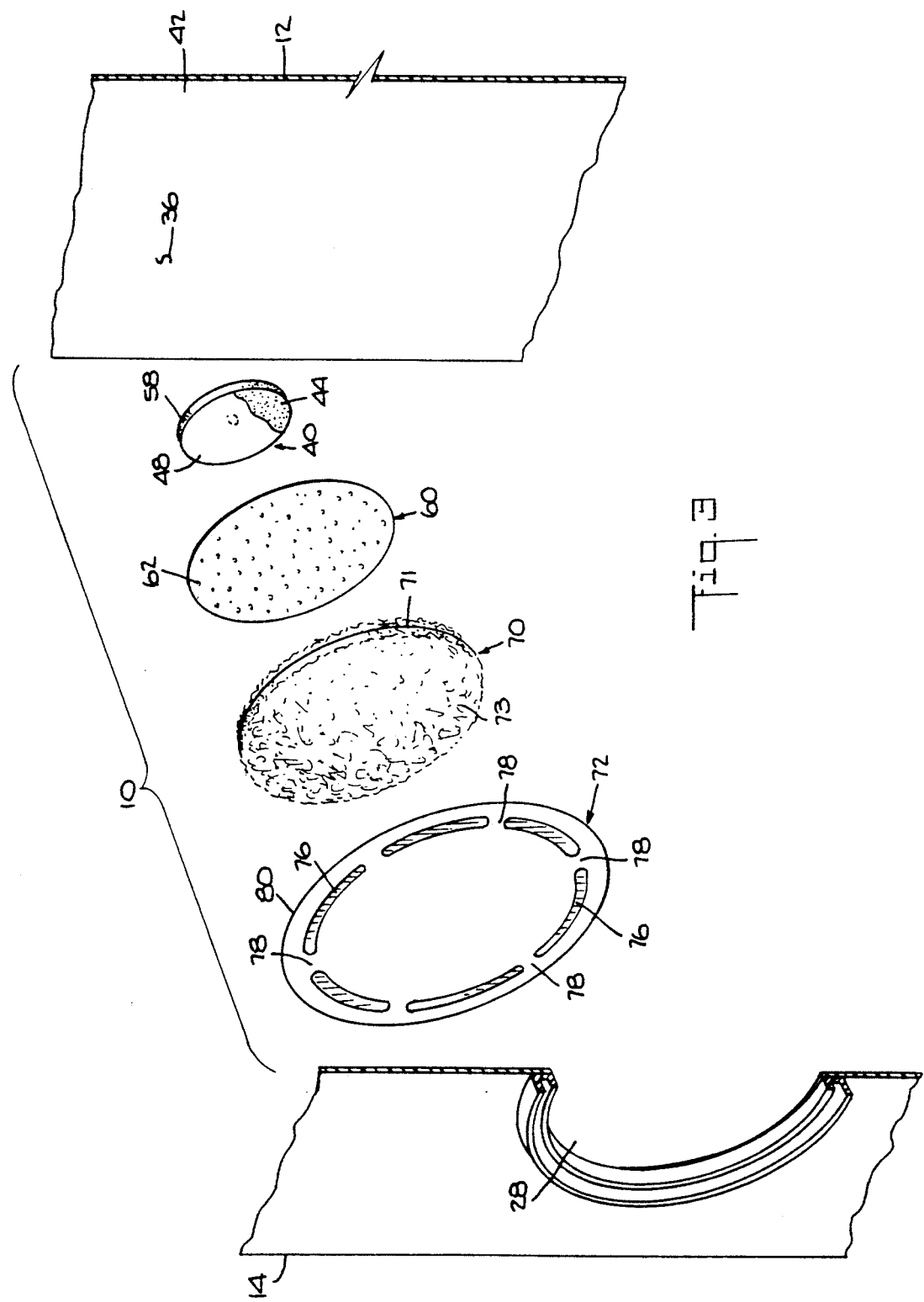

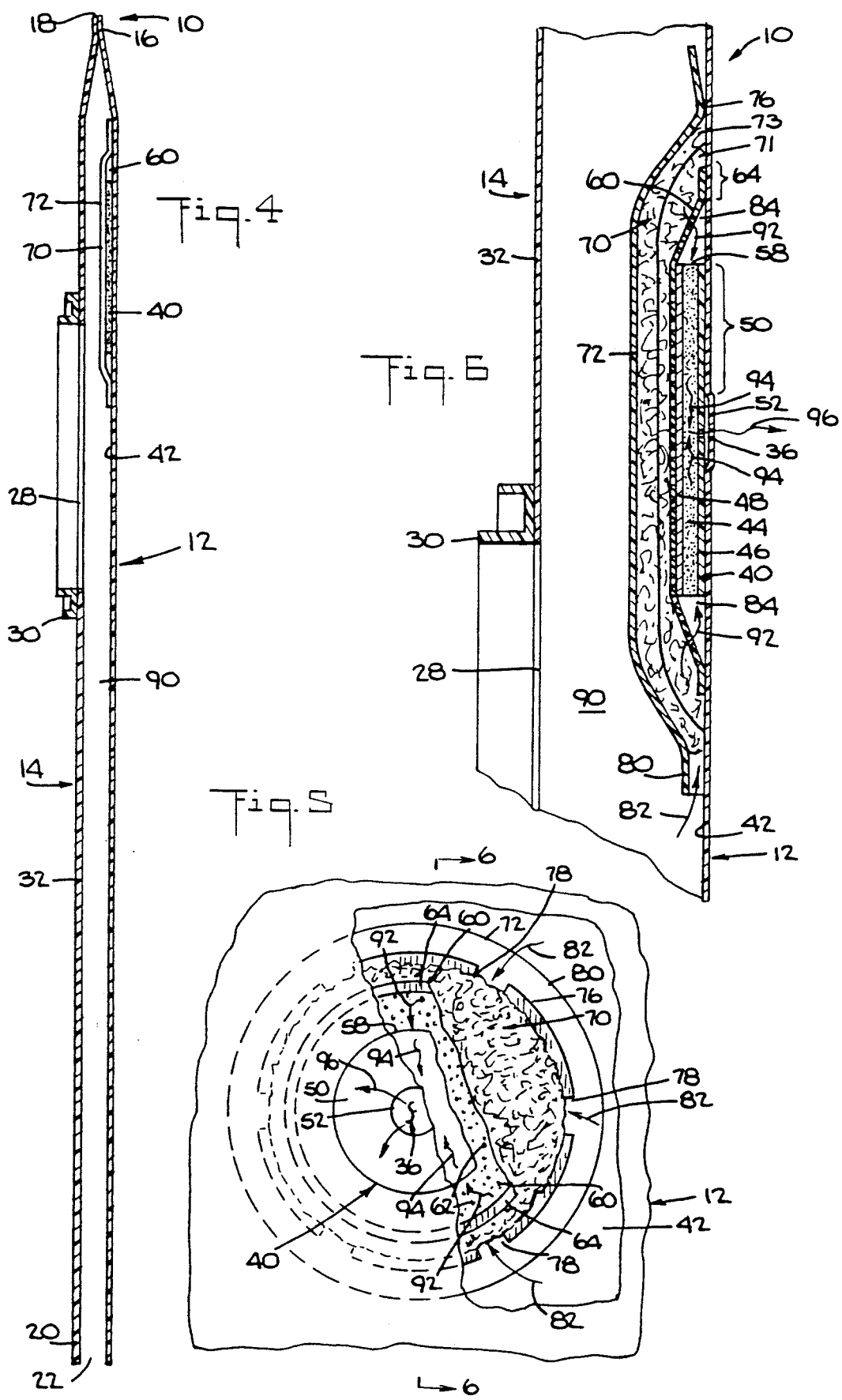

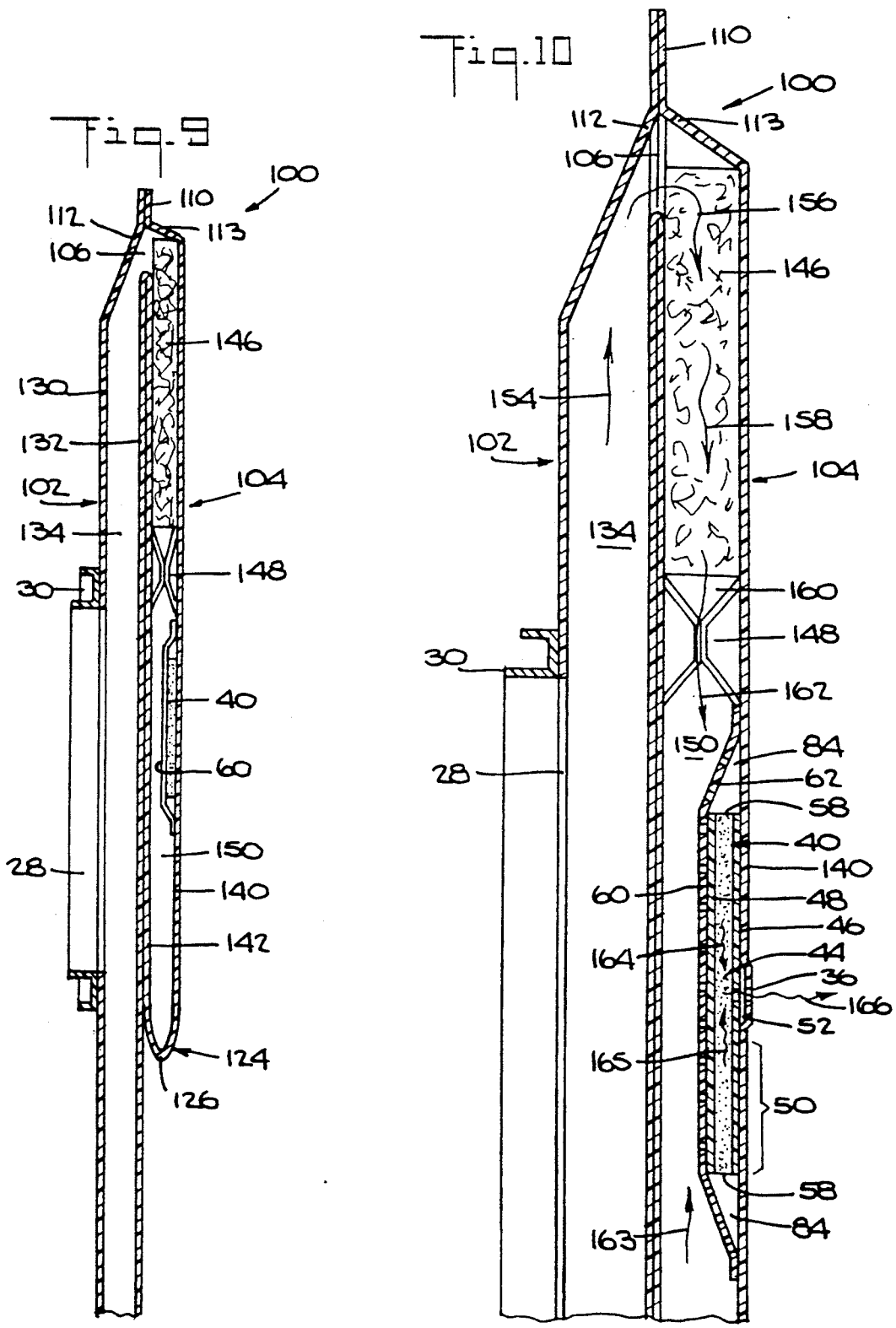

OSTOMY BAG WITH MULTI-STAGE FILTER

BACKGROUND OF THE INVENTION

This invention is directed to ostomy bags and more particularly to an ostomy bag with a novel multi-stage filter that resists contact contamination by semi-liquid waste collected in the bag.

Gases emitted from the stoma into an ostomy bag and gases that issue from waste material confined in the bag are usually evacuated through a deodorizing filter. A gas outlet is thus provided in the ostomy bag, normally adjacent the deodorizing filter to ensure that the outward flow of gas passes through the filter.

Most ostomy bags can generally be worn a few days before the deodorizing capability of the filter begins to lose effectiveness. The exhausted filter can then be replaced if the bag has provision for replaceable filters as in ostomy bags of U.S. Pat. No. 5,085,652. If there is no provision for filter replacement as in the ostomy bag of U.S. Pat. No. 5,074,851, the entire bag is disposed of and replaced when the filter is no longer an effective deodorizer.

If the deodorizing filter is inadvertently contaminated by contact with waste material that accumulates in the bag, it may be desirable to replace the disposable bag immediately. Waste material contact with a deodorizing filter can occur as a result of physical activity by the wearer that shifts the contents of the bag toward the deodorizing filter, especially if such waste material is of a liquid or semi-liquid consistency.

Contact of the deodorizing filter with semi-liquid waste material will often clog the filter, thereby preventing adequate deodorization and evacuation of waste gas. Whenever a filter is contaminated by contact with semi-liquid waste material and such contamination impedes the function of the filter, the filter or bag should be replaced as soon as possible. The need for accelerated replacement of deodorizing filters and/or ostomy bags because of contact contamination by waste is usually an inconvenience to the wearer.

Filter contamination from contact with semi-liquid waste also commonly occurs when an individual is asleep or reclining because the ostomy bag is in a relatively horizontal orientation. In such instances, gas pressure may build up in the bag because of the lowered rate of gas evacuation due to filter clog. Pressure release can thus occur through an undesirable break in the bag seal at the stoma. If the leak or seal break is not detected, it can result in the soiling of an individual's garments.

It is thus desirable to provide an ostomy bag with a multi-stage filter system that prevents semi-liquid waste material from contaminating a deodorizing element but does not inhibit evacuation of gaseous waste through the deodorizing element.

OBJECTS AND SUMMARY OF THE INVENTION

Among the several objects of the invention may be noted the provision of a novel ostomy bag, a novel ostomy bag with a protective device for a deodorizing element which prevents semi-liquid waste material from contaminating the deodorizing element while permitting gaseous waste material to pass through the deodorizing element, a novel ostomy bag with a novel multi-stage filter system for gas deodorizing that enables a deodorizing element to resist contact contamination by semi-liquid waste material, a novel ostomy bag having dual chambers with one chamber containing a stoma engagement opening and the other chamber containing a gas deodorizing filter, a novel ostomy bag which has a semi-liquid waste collection chamber and a gas outlet chamber with protection against semi-liquid waste reaching a gas deodorizing filter therein, and a novel method of preventing contamination of a gas deodorizing filter.

Other objects and features of the invention will be in part apparent and in part pointed out hereinafter.

In accordance with the invention, the multi-stage filter includes a gas transmissive protection device for a deodorizing element that is impassible to semi-liquid waste material. The gas transmissive protection device precedes the deodorizing element or filter such that gaseous waste must pass through the protection device before it passes through the filter.

In one embodiment of the invention, the multi-stage filter includes a deodorization filter intended to remove odor, a microporous protection film intended to protect the deodorizing filter from liquids, an open cell foam barrier to protect the microporous film from semi-solid fluids and liquids, and a plastic fluid-impermeable film cover with gas passages that substantially encases the other stages of the multi-stage filter. The film cover is intended to protect the other stages from the bulk of the semi-solid liquids and allow gas to pass through the gas passages. Thus, the fluid-impermeable film cover is bonded along a discontinuous bond line, with the discontinuities providing access paths for gas to flow through the succeeding stages to the deodorizing filter for eventual evacuation from the ostomy bag.

In another embodiment of the invention the ostomy bag is a dual chamber structure with one chamber provided with a waste inlet opening to receive semi-liquid waste and gaseous waste. The other chamber is provided with a gas outlet and a multi-stage filter having a deodorizing element. The chambers are communicable, through a communication port or opening, for example.

A multi-stage filter that is ga transmissible but impassible to semi-liquid and semi-solid fluid waste is provided in the gas outlet chamber. The multi-stage filter includes an open cell foam barrier placed across the gas outlet chamber, preferably across the communication opening and the gas outlet chamber. The foam barrier does not overlay the deodorizing filter but is at a different level so as to precede the deodorizing filter relative to the flow path of gaseous waste through the deodorizing filter. Thus gaseous waste must pass through the foam barrier before it passes through the deodorizing filter.

The multi-stage filter further includes a microporous protection film surrounding the deodorizing element or filter.

In either embodiment the multi-stage filter is impassible to semi-liquid waste material but permits gaseous waste to pass through. Thus the deodorizing filter is protected from being contacted by semi-liquid waste material The deodorizing filter, by avoiding clogging contact with semi-liquid waste material can operate for its rated life and thereby enable the ostomy bag to be used for a normal duration period before filter replacement or bag replacement is required.

The invention accordingly comprises the constructions and method hereinafter described, the scope of the invention being indicated in the claims.

DESCRIPTION OF THE DRAWINGS

In the accompanying drawings,

FIG. 1 is a simplified schematic plan view of one side of an ostomy bag incorporating one embodiment of the invention;

FIG. 2 is a simplified schematic plan view of the reverse side thereof;

FIG. 3 is an enlarged fragmentary, exploded perspective view thereof;

FIG. 4 is a section view taken on the line 4—4 of FIG. 5 is a partly broken enlarged fragmentary plan view thereof;

FIG. 6 is a section view taken on the line 6—6 of FIG. 7 is a simplified schematic plan view of one side of another embodiment of the invention;

FIG. 9 is a section view taken on the line 9—9 of FIG. 7; and,

FIG. 10 is an enlarged fragmentary section of FIG. 9.

Corresponding reference characters indicate corresponding parts throughout the several views of the drawings.

DETAILED DESCRIPTION OF THE INVENTION

Figure 8:
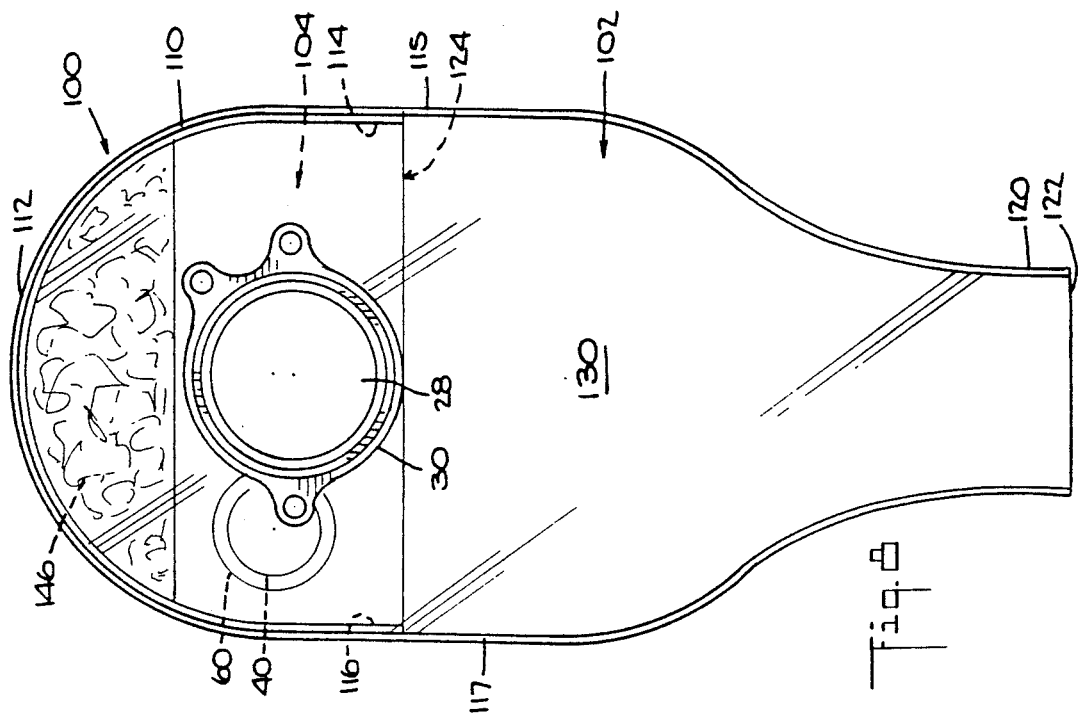
FIG. 8 is a simplified schematic plan view of the reverse side thereof.
Figure 7:
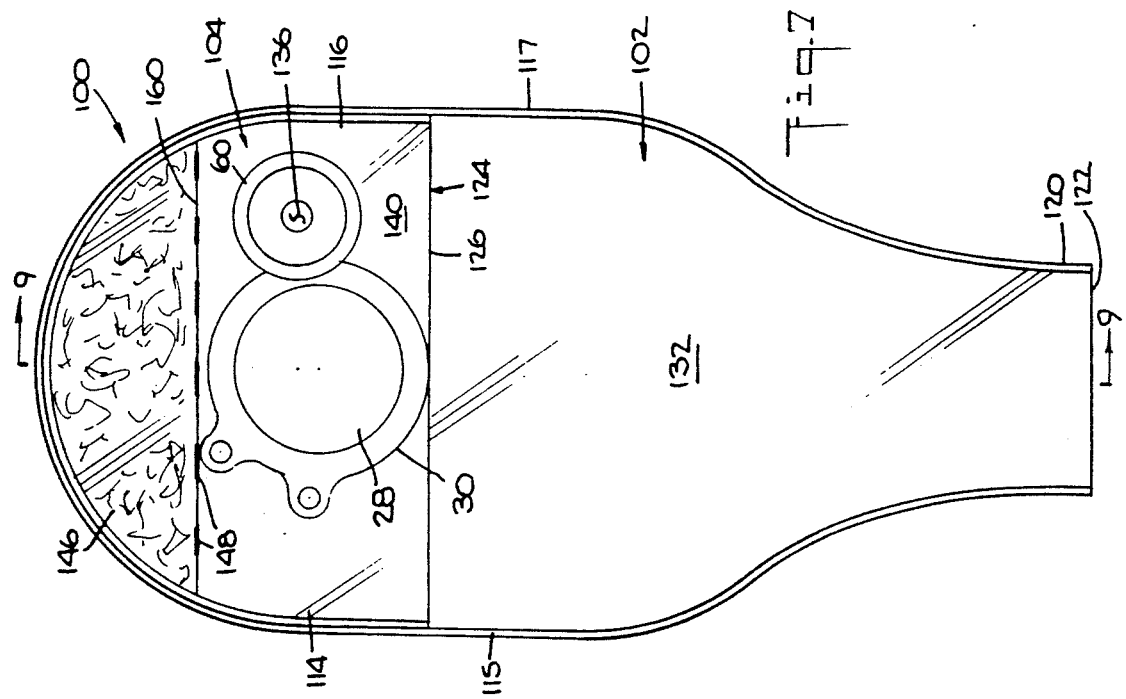

An ostomy bag incorporating one embodiment of the invention is generally indicated by the reference number 10 in FIG. 1. The ostomy bag is formed of a suitable known thermoplastic material that is gas impermeable, flexible and expandable.

The bag 10 includes a front wall 12 that faces away from the abdomen, and a rear wall 14 that confronts the abdomen, joined together by a peripheral thermoweld 16. The walls 12 and 14 are approximately 40 to 100 microns thick. The bag 10 further includes a top portion 18, a bottom portion 20 with a reclosable open end 22, and opposite side portions 24 and 26. A reusable clamp (not shown) is provided at the bottom portion 20 to open and close the open end 22.

A stoma engagement opening 28 is formed in the rear wall 14 nearer the top portion 18 of the bag 10 than the bottom portion 20. The stoma engagement opening 28 is bordered by a known flexible plastic coupling flange 30 in the form of a ring joined to an outside surface 32 of the rear wall 14 in any suitable known manner. The coupling flange 30 interlocks with a known interlocking ring flange (not shown) that is provided around the stoma.

An S-shaped gas evacuation slit 36 (FIG. 3) is formed in the front wall portion 12 of the bag 10 near the top and side edges 18 and 24, offset from the stoma engagement opening 28.

A generally circular deodorizing filter 40 of the type sold under the designation Freudenberg Code 9347 by Freudenberg Industrial of West Yorkshire, England, is provided at an inside surface 42 of the front wall 12 in substantial alignment with the gas evacuation slit 36. The filter 40 includes a filtration layer 44 (FIG. 6) formed of polyurethane foam containing activated carbon sandwiched between cover layers 46 and 48. The cover layer 46 is gas permeable and formed of microfine nonwoven material with a layer of hot melt adhesive, whereas the cover layer 48 is gas semi-permeable microporous film. Preferably the filter is approximately 24.4 mm.±1 mm. in diameter and 2 to 3 mm. thick.

The filter 40 is joined to the inside surface 42 of the front wall 12 at a peripheral gas impermeable bonding zone 50 (FIGS. 5 and 6) of the cover layer 46. Heat is applied to the hot-melt adhesive layer at the bonding zone 50 to provide a bond width of approximately 8.6 mm. Thus a central circular unbonded area 52 of approximately 7.1 mm in diameter is defined in the gas permeable cover layer 46 within the confines of the bonding zone 50. The unbonded area 52 confronts the evacuation slit 36 in the front wall 12.

Since the cover layer 48 of the filter 40 is gas semipermeable, gas can only enter the filter 40 at a peripheral edge 58 of the filter 40 (FIGS. 5 and 6).

A porous film 60 formed of ethylene vinyl acetate and provided with a plurality of microporous holes 62 (FIG. 3) approximately 4-5 mm. in diameter, is also joined to the front wall 12 of the bag at the inside surface 42 along a peripheral bonding zone 64 (FIGS. 5 and 6) that encircles the filter 40.

A protection filter 70, preferably formed of open cell polyurethane foam of the type made by Foamex under the commercial name Protectaire-Z is sandwiched between the porous film 60 and a fluid impermeable film wafer 72 formed of polyethylene. The protective filter 70 can be of one pore size such as 40 pores per inch, or the filter can be a dual layer arrangement with two pore sizes. The stacked arrangement is preferred and includes a layer 71 adjacent the porous film 60 and having approximately 45 pores per inch with a pore diameter of approximately 45 mm. The filter 70 also includes a layer 73 adjacent the layer 71 approximately 3.2 mm. thick and having approximately 30 pores per inch with a pore diameter of approximately 45 mm.

The fluid impermeable film wafer 72 is joined to the inside surface 42 of the front wall 12 at a discontinuous peripheral bonding zone 76 that encircles the porous film 60. Preferably six equally spaced discontinuities 78 are provided in the bonding zone 76 and are approximately 50 mm. in extent.

In operation of the ostomy bag 10, the coupling flange 30 is engaged with a ring-shaped mating coupling flange (not shown) provided around the stoma. The coupling flange engagement forms a substantially leak-tight seal between the bag 10 and the stoma. The open end 22 of the bottom portion 20 is clamped shut in leak-tight fashion using any suitable known releasable clamp (not shown).

Semi-liquid and gaseous waste material (not shown) are thus allowed to enter a collection chamber 90 (FIG. 6) defined between the front and rear walls 12 and 14 of the bag 10. The semi-liquid waste and gaseous waste accumulate in the collection chamber 90 with the gaseous waste being evacuated through the deodorizing filter 40 and the gas outlet 36.

Before the waste gas reaches the deodorizing filter 40 and the gas outlet 36, it must pass through the discontinuities 78 in the bonding zone 76 of the film wafer 72. A peripheral edge 80 of the film wafer 72 is left unbonded as most clearly shown in FIG. 6, to provide a path for the waste gas to enter the discontinuities 78, as for example, along a path indicated by the arrow 82.

As most clearly shown in FIG. 5, the protection filter 70 is in the path of the discontinuities 78. The filter 70 will thus block the passage of semi-liquid waste material because the filter 70 provides a tortuous path of decreasing pore size that cannot be negotiated by the semi-liquid waste. The filter also causes bubbles of fluid to form by surface tension. The bubbles of fluid cling to the foam and interrupt the flow of the semi-liquid waste. Body motion by the user results in an ongoing breaking and reforming of the surface tension bubbles which provides a path for the gas to travel. The semi-liquid waste does not clog the film wafer 72 because of the size and number of the discontinuities 78.

The waste gas thus passes through the protective filter 70 and through the pores 62 of the porous protection film 60 into an annular peripheral space 84 in the direction indicated by the arrows 92 in FIG. 6. Since a circular portion of the porous protection film 60 bounded by the peripheral space 84 is blocked by the gas impermeable cover layer 48 of the filter 40, the waste gas is directed toward the periphery 58 of the filter 40 in the direction indicated by the arrow 92.

Gas flow is then directed into the filtration layer 44 as indicated by the arrows 94 in FIG. 6, toward the central unbonded area 52 between the filter 40 and the front wall 12. The gas outlet slit 36, which aligns with the unbonded area 52, provides an evacuation point for the waste gas to exit from the bag 10 to the outside as indicated by the arrow 96. Under this arrangement, the filter 40 is protected by the filter 70 from contact with semi-liquid waste material since the filter 70 is impassable by semi-liquid waste but does not impede the flow of gaseous waste.

The multi-stage filter system thus includes a series of components namely the deodorizing filter 40, the film 60, the filter 70 and the film 72, that provide contamination protection for the deodorizing filter 40. The components work together to provide effective deodorization of flatus and extend the life of the deodorization filter 40.

Another embodiment of the ostomy bag is generally indicated by the reference number 100 in FIGS. 7-10.

Referring to FIGS. 9 and 10, the ostomy bag 100 includes a pair of adjacent chamber sections 102 and 104 that communicate with each other through a communication port 106. The chamber sections 102 and 104, which are commonly joined at the top and sides by a peripheral thermoweld 110, have adjacent top portions 112 and 113. Relatively short side portions 114 and 116 of the chamber section 104 overlap relatively long side portions 115 and 117 of the chamber section 102.

The chamber section 102 has a bottom portion 120 with an open end 122 that is normally maintained in a closed position by a removable clamp (not shown). The chamber section 104 has a bottom portion 124 with a permanently sealed closed end 126. As most clearly shown in FIGS. 7 and 8, the bottom portion 124 is elevated from the bottom portion 120 since the chamber section 104 is of shorter extent than the chamber section 102. It will be noted that the bottom portion 124, which is rearwardly disposed in FIG. 8, is shown in solid line because the bag 100 is preferably transparent.

Referring to FIGS. 9 and 10, the chamber section 102 has spaced walls 130 and 132 which define a waste collection chamber 134. The wall 130 is provided with a stoma engagement opening 28 surrounded by a coupling flange 30.

The chamber section 104 includes spaced walls 140 and 142 which define a gas outlet chamber 150. The walls 142 and 132, which are adjacent, need not be bonded together except at the peripheral thermoweld 110. The wall 132 is shorter at the top portion 112 than the wall 130 and the wall 142 is shorter at the top portion 113 than the wall 140 by the same amount as the wall portion 132 to provide the communication port 106.

An S-shaped gas outlet slit 36 (FIG. 7) is formed in the wall portion 140. A filter 40 is aligned with the gas outlet slit 36 and backed up by a porous protection film 60 in the same manner as previously described for the filter 40 of the bag 10.

A protective filter 146 formed of the same open cell material as the protective filter 70 having approximately 40 pores per inch with a pore diameter of approximately 45 mm. The filter 146 is disposed across the chamber 150 from the wall 140 to the wall 142 near the top portion 113 in the area of the communication port 106. If desired, the protective filter 146 can be disposed across the communication port 106 so as to cover the port. The protective filter 146 is thus situated to precede the gas deodorizing filter 40 relative to the outlet flow path of gaseous waste through the deodorizing filter 40 such that any gas flow through the communication port 106 must pass through the protective filter 146 before it reaches the deodorizing filter 40. If desired, the filter 146 can also be formed as a two layer structure in the manner described for the filter 70.

A plurality of spaced thermowelds 148 (FIGS. 1, 9 and 10) between the wall portions 140 and 142, fix the position of the protective filter 146 relative to the filter 40 such that no portion of the protection filter 146 overlaps the deodorizing filter 40.

In operation of the ostomy bag 100, the coupling flange 30 is engaged with a mating coupling flange (not shown) provided around the stoma to form a substantially leak-tight seal. The open end 122 of the chamber section 102 at the bottom portion 120 is clamped shut in leak-tight fashion using any suitable known releasable clamp (not shown). Semi-liquid and gaseous waste material (not shown) is thus allowed to enter the collection chamber 134 through the stoma engagement opening 28.

Semi-liquid waste and gaseous waste accumulate in the collection chamber 134 with the gaseous waste flowing into the gas outlet chamber 150 in the direction indicated by the arrow 154 (FIG. 10) for evacuation through the deodorizing filter 40 and the gas outlet 36.

Before the confined gaseous waste reaches the deodorizing filter 40 and the gas outlet 36, it must pass through the communication port 106 where it encounters the protective filter 146. The gaseous waste flows along a path defined by the arrows 156 and 158 through the protective filter 146 and through spaces 160 between the thermowelds 148 as indicated by the arrow 162.

The gaseous waste fills the remainder of the chamber 150 below the protective filter 146 as indicated at the arrow 163 in FIG. 10. Gaseous waste then passes through the pores 62 of the protection film 60 into an annular peripheral space 84 surrounding the filter 40 and into the peripheral edge 58 of the filter 40 where the gas enters the filtration layer 44. Gas flows through the filtration layer 44 toward the center of the filter 40 as indicated by the arrows 164 and 165 for exit through the central unbonded area 52 where it is evacuated to the outside through the gas outlet 36 as indicated at the arrow 166.

Should semi-liquid waste reach the communication port 106, it is blocked from passing through by the protective filter 146 for the same reasons described with respect to the filter 70. Thus there is no accumulation of semi liquid waste material in the filter 146 which would block passage of gaseous waste. The protective filter 146 essentially isolates the filter 40 from semi-liquid waste material and thus protects the filter 40 from contamination by the semi-liquid waste material.

As will be apparent to those skilled in the art, the arrangement of the protective filter 70 over the deodorizing filter 40 in the ostomy bag 10 or the arrangement of the protective filter 146 across the gas outlet chamber 150 and/or communication port 106 of the ostomy bag 100, is also adaptable to most types of ostomy bags including those that do not have bottom openings.

Some advantages of the invention evident from the foregoing description include an ostomy bag with a multi-stage filter system that provides contamination protection for a deodorizing filter and helps assure against inadvertent premature contamination of the deodorizing filter by semi-liquid waste material accumulated in the bag. A further advantage of the ostomy bag is that the multi-stage filter system enables the user to engage in activities or body postures that may shift the contents of the bag, without fear that such activities will cause contamination of the deodorizing filter. A further advantage of the invention is that the ostomy bag can be reliably worn for its normal rated life because the deodorizing filter is not likely to be prematurely contaminated by semi-liquid waste material.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An ostomy bag for holding body waste that passes through a stoma comprising,
   (a) an envelope formed of flexible plastic sheet material defining a waste collection chamber for body waste that includes gaseous and semi-liquid waste material, said envelope having interior surface portions and a top end portion,
   (b) a waste inlet opening formed in said envelope proximate said top end portion, said waste inlet opening being of predetermined size and including means for fitting said opening around a stoma,
   (c) gas outlet means formed in said envelope proximate said top end portion and spaced from said waste inlet opening,
   (d) a deodorizing filter joined to said envelope in alignment with said gas outlet means for deodorizing gaseous waste material before said gaseous waste material exits from said bag through said gas outlet means, and
   (e) means for protecting said deodorizing filter from contact by semi-liquid waste material, and for permitting the flow of gaseous waste, and for preventing the flow of semi-liquid waste, said protection means including open-cell foam material, said protection means being located in said envelope to precede the deodorizing filter such that the gaseous waste must pass through said protection means before it passes through said filter.

2. An ostomy bag as claimed in claim 1 wherein said protection means overlaps said filter.

3. An ostomy bag as claimed in claim 2 wherein said protection means shrouds said filter.

4. An ostomy bag as claimed in claim 3 wherein a cover layer covers said protection means, said cover layer being substantially impervious to fluid, said cover layer being joined to said envelope by a discontinuous bond to provide fluid entry ports at the bond discontinuities, said fluid entry ports permitting waste gas to bypass the cover layer and pass through said protection means for subsequent passage through said filter.

5. An ostomy bag as claimed in claim 4 wherein said filter has a fluid impervious face confronting said protection means and a fluid previous peripheral edge such that gaseous waste passing through said protection means can only enter said filter at said fluid previous peripheral edge.

6. An ostomy bag as claimed in claim 1 wherein said protection means is spaced from said filter such that no part of said protection means overlaps said filter.

7. An ostomy bag as claimed in claim 6 wherein said envelope includes a gas outlet chamber adjacent said waste collection chamber and communicable with said waste collection chamber, said waste inlet opening being provided at said waste collection chamber and said filter being provided in said gas outlet chamber, said protection means being provided in one of said chambers.

8. An ostomy bag as claimed in claim 7 wherein said protection means is provided in said gas outlet chamber.

9. An ostomy bag as claimed in claim 8 wherein said protection means is disposed between the top end portion of said envelope and said filter such that no part of said protection means overlaps said filter.

10. An ostomy bag as claimed in claim 7 wherein said waste collection chamber and said gas outlet chamber are communicable at the top end portion of said envelope.

11. An ostomy bag as claimed in claim 10 wherein said waste collection chamber and said gas outlet chamber communicate through a communication port in said envelope, said protection means extending across said communication port.

12. An ostomy bag as claimed in claim 7 wherein said gas outlet chamber is of smaller volume than said waste collection chamber.

13. An ostomy bag as claimed in claim 1 wherein said open cell foam material includes a first layer having approximately 30 pores per inch, and a second adjacent layer having approximately 45 pores per inch, arranged such that gaseous waste passes through said first layer before it passes through said second layer.

14. An ostomy bag as claimed in claim 1 wherein said open cell foam material is a single layer having 40 pores per inch.

15. An ostomy bag for holding body waste passing through a stoma comprising,
   (a) an envelope formed of flexible plastic sheet material defining a collection space for body waste including gaseous and semi-liquid waste material, said collection space including two adjacent communicable chamber sections communicable through a communication opening in said envelope, said chamber sections having interior surface portions,
   (b) a waste inlet opening formed in one of said chamber sections and including means for fitting said waste inlet opening around a stoma,
   (c) gas outlet means formed in the other of said chamber sections to evacuate gaseous waste from said collection space, (d) a deodorizing filter in said other chamber section for deodorizing gaseous waste before it is evacuated through said gas outlet means, said deodorizing filter being joined to said envelope in alignment with said gas outlet means, and (e) gas transmissive protection means for protecting said filter from contact by semi-liquid waste material, said protection means including an open-cell foam material, said protection means being located in one of said chamber sections to precede the deodorizing filter such that gaseous waste within said collection space must pass through said protection means before it passes through said deodorizing filter.

16. An ostomy bag for holding body waste passing through a stoma comprising, (a) an envelope formed of flexible plastic sheet material, said envelope including two adjacent communicable chamber sections communicable through a communication opening in said envelope, (b) one of said chamber sections being formed with a waste inlet opening and means for fitting said waste inlet opening around stoma, (c) the other of said chamber sections being formed with a gas outlet through which gaseous waste is evacuated, (d) a deodorizing filter in said other chamber section for deodorizing gaseous waste material before it is evacuated through said gas outlet, said filter being joined to said envelope in alignment with said gas outlet, and (e) gas transmissive protection means in said other chamber for protecting said deodorizing filter from contact by semi-liquid waste material, said protection means including open-cell foam material.

17. An ostomy bag as claimed in claim 16 wherein said other chamber is of lesser volume than said one chamber section.

18. A method of preventing contamination of a gas deodorizing filter in an ostomy bag comprising, (a) forming a waste gas outlet in a wall of the bag, (b) bonding a waste gas deodorizing filter to the inside of the bag in alignment with the gas outlet, (c) covering the deodorizing filter with a protection filter that resists passage of semi-liquid waste but permits passage of gas waste, (d) forming a gas transmissible protection filter including an open-cell foam material, that is impassible to semi-liquid waste and locating the protection filter in the bag to precede the deodorizing filter such that gaseous waste in the bag must pass through the protection filter before it enters the deodorizing filter.

19. The method of claim 18 including covering the deodorizing filter with the protection filter.

20. The method of claim 18 including locating the deodorizing filter and the waste inlet opening in separate chamber sections of the bag that communicate with each other through a communication opening and providing the protection filter in one of the chamber sections.

* * * * *